(12) United States Patent
Commerford (10) Patent No.: US 9,068,343 B2
(45) Date of Patent: Jun. 30, 2015

(54) CONSTRUCTION ELEMENT

(71) Applicant: Termite Solutions Victoria Pty Ltd., Bentleigh, Victoria (AU)

(72) Inventor: Paul Anthony Commerford, Bentleigh (AU)

(73) Assignee: TERMITE SOLUTIONS VICTORIA PTY LTD., Bentleigh, Victoria (AU)

( * ) Notice: Subject to any disclaimer, the term of this patent is extended or adjusted under 35 U.S.C. 154(b) by 0 days.

(21) Appl. No.: 13/716,345

(22) Filed: Dec. 17, 2012

(65) Prior Publication Data

US 2013/0111838 A1    May 9, 2013

Related U.S. Application Data

(63) Continuation-in-part of application No. PCT/AU2010/001359, filed on Oct. 14, 2010.

(30) Foreign Application Priority Data

Jun. 22, 2010    (AU) ................................ 2010902706

(51) Int. Cl.
| | |
|---|---|
| *B32B 7/12* | (2006.01) |
| *B32B 7/06* | (2006.01) |
| *B32B 5/18* | (2006.01) |
| *E04B 1/72* | (2006.01) |
| *A01N 25/16* | (2006.01) |
| *A01N 25/34* | (2006.01) |
| *A01M 29/12* | (2011.01) |
| *A01M 29/34* | (2011.01) |

(52) U.S. Cl.
CPC . *E04B 1/72* (2013.01); *A01N 25/16* (2013.01); *A01N 25/34* (2013.01); *B32B 5/18* (2013.01); *B32B 7/06* (2013.01); *B32B 7/12* (2013.01); *B32B 2255/102* (2013.01); *B32B 2260/00* (2013.01); *B32B 2266/02* (2013.01);

(Continued)

(58) Field of Classification Search
CPC .......... E04B 1/72; A01M 29/34; A01M 29/12; B32B 5/18; B32B 7/12; B32B 7/06; B32B 2307/764; B32B 2255/102; B32B 2260/00; B32B 2266/02; B32B 2419/00; A01N 25/34; A01N 25/16
USPC ............................ 428/352, 314.4, 314.8, 343
See application file for complete search history.

(56) References Cited

U.S. PATENT DOCUMENTS

| | | | | |
|---|---|---|---|---|
| 6,156,328 | A * | 12/2000 | Alcott et al. ................... | 424/405 |
| 7,603,816 | B1 * | 10/2009 | Hohmann, Jr. .................. | 52/101 |

(Continued)

FOREIGN PATENT DOCUMENTS

EP    1 159 875 A1    12/2001

OTHER PUBLICATIONS

EP search report, Nov. 24, 2014.

(Continued)

*Primary Examiner* — Jessica Laux
(74) *Attorney, Agent, or Firm* — Vedder Price P.C.; Thomas J. Kowalski; Deborah L. Lu (57) ABSTRACT

A construction element for forming an expansion joint, wherein the construction element acts as a physical and chemical barrier against the penetration of insects, in particular termites, into a structure, the construction element comprising a closed cell polymeric foam containing at least one insecticide substantially distributed throughout the polymeric foam; wherein on at least one outer surface of the construction element there is a water resistant adhesive attached thereto and a removable cover releasably attached to the adhesive whereby the removable cover is adapted to be removed upon application of the casting element.

22 Claims, 4 Drawing Sheets

(52) U.S. Cl.
CPC ....... *B32B2307/764* (2013.01); *B32B 2419/00* (2013.01); *A01M 29/12* (2013.01); *A01M 29/34* (2013.01)

(56) References Cited

U.S. PATENT DOCUMENTS

| | | | |
|---|---|---|---|
| 8,015,757 B1 * | 9/2011 | Hohmann, Jr. | .................. 52/101 |
| 2001/0000371 A1 | 4/2001 | Traxler | |
| 2006/0234033 A1 * | 10/2006 | Nishikawa et al. | ......... 428/314.8 |
| 2009/0169860 A1 * | 7/2009 | Katsunori et al. | ......... 428/314.8 |

OTHER PUBLICATIONS

Extended European Search Report dated Nov. 24, 2014 (includes, pursuant to 62 EPC, the supplementary European search report (Art. 153(7) EPC) and the European search opinion).

* cited by examiner

FIGURE 1

Termite barrier:

CONSTRUCTION ELEMENT

RELATED APPLICATIONS AND INCORPORATION BY REFERENCE

This application is a continuation-in-part application of international patent application Ser. No. PCT/AU2010/001359 filed 14 Oct. 2010, which published as PCT Publication No. WO 2011/160158 on 29 Dec. 2011, which claims benefit of Australian patent application Ser. No. 2010902706 filed 22 Jun. 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to the control of termites in relation to buildings and other structures, in particular, the present invention relates to a construction element useful for the building, construction and pest control industries.

BACKGROUND OF THE INVENTION

Buildings and other structures are susceptible to entry by insects. Some insects, such as termites, can damage the building and potentially lead to a loss in structural integrity. In general, termites enter the building where it contacts the ground. From there, the termites may spread rapidly throughout the building, causing significant damage to any timber.

Physical barriers have been employed to guard against the concealed entry of insects, particularly termites to buildings. Typically, these barriers are in the form of plastic sheets, stainless steel mess or graded stone materials and are placed in accordance with specifications outlined in Australian Standard 3660-2, 2000 (and comparable international standards) and manufacturers instructions.

Generally this includes the perimeter edge, construction joins and penetrations (for example electrical conduit, plumbing, other services and any other planned or unplanned protrusion through the concrete slab creating ground contact) of concrete slab construction and the perimeter base level brickwork of subfloor constructions. In some instances the entire under slab area is treated using a combined damp proof and termite barrier plastic sheet material.

In some states liquid chemical treatments using a number of different approved termiticides are an acceptable alternative to the use of physical termite barriers.

The installation of a termite barrier is in many states a regulated building practice with installers required to certify that a termite management system has been installed.

Concrete structures are subjected to a variety of stresses are the result of shrinkage and differential movement. Shrinkage occurs during hydration, and differential movement caused by temperature changes and different loading conditions. These stresses can cause cracking, spalling, and scaling of concrete surfaces and, in extreme cases, can result in the failure of the structure.

Stresses in concrete can be controlled somewhat by the proper placement of a concrete compressible material in the construction joints between slab pours, around any service penetrations and against any infill slab structures.

The compressible, concrete casting material commonly referred to as expansion joint foam or lagging absorbs pressure and allows for the expansion and contraction of the slab against existing construction elements over time to avoid cracking or other damage to the slab.

The aforementioned construction details including but not limited to service penetrations, construction joins and perimeter edges of slabs are all areas where concealed entry by termites may occur.

The installation of expansion joint foams is an expected building practice.

When installing a physical barrier such as Kordon Termite Barrier (Kordon TB), Homeguard, Trithor or Termseal it is often necessary to remove foam expansion joint strips and lagging to install the barrier and then replace the expansion joint stripping or lagging again. This duplicated effort is unnecessary.

Difficulties faced in installing the above products also include applying them on exposed work sites where they were affected by inclement weather such as high winds, rain and pooling of water. The current systems use a variety of systems including adhesives applied using a caulking gun or concrete nails to attach the termite barriers to the required areas.

Most termite systems therefore require the use of multiple products to create a complete and compliant, system, therefore installers have had to stock a range of tools and materials.

The installation process of existing physical products and chemical barriers requires the engagement of licensed pest controller. This usually requires the scheduling of works in conjunction with a builders often fluctuating construction schedule especially as it relates to the preparation of concrete slabs and tilt panel lifts. It was often considered a nuisance or hassle to have to liaise with and schedule the licensed pest controller to be on site when required and often led to critical delays in the construction scheduling.

Citation or identification of any document in this application is not an admission that such document is available as prior art to the present invention.

SUMMARY OF THE INVENTION

It is therefore desirable to provide a construction element which at least alleviates some of the problems identified above.

The present invention provides a construction element for forming an expansion joint, wherein the construction element acts as a physical and chemical barrier to impede the ingress of insects into a structure, the construction element which may comprise a polymeric foam containing at least one insecticide substantially distributed throughout the polymeric foam;
wherein the polymeric foam has a cell size of approximately 0.5 to 2 mm; and
wherein on at least one outer surface of the construction element there is a water resistant adhesive attached thereto and a removable cover releasably attached to the adhesive whereby the removable cover is adapted to be removed upon application of the construction element.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
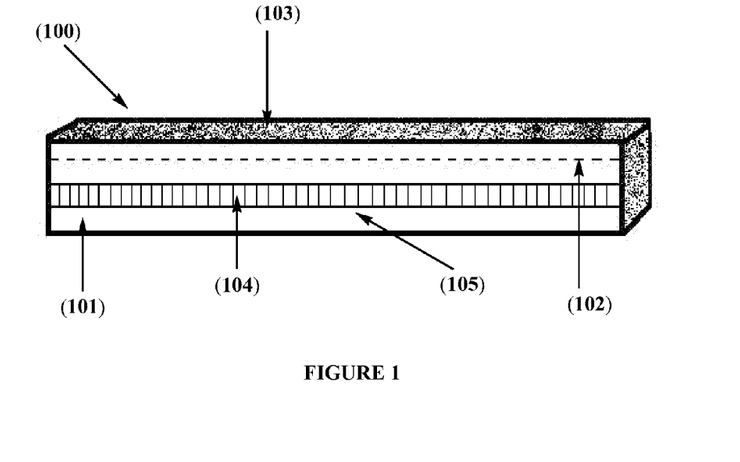
FIG. 1: Illustration of the construction element according to one embodiment of the present invention
Figure 1A:
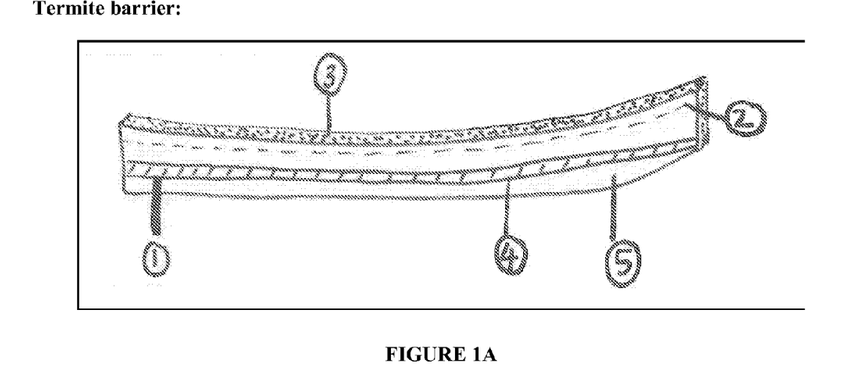
FIG. 1A: Illustration of a construction element according to an embodiment of the present invention

Referring to FIG. 1 a cross section of a construction element (100) is shown which acts as both a physical and chemical barrier to impede the penetration of insects through a concrete slab. In this example, the construction element is made from a closed cell polymeric foam impregnated (101) with an insecticide (103), for example bifenthrin. The construction element could also be made using an open celled polymeric foam. A zipping strip (102) along one top edge of the element can be used to create a neat finish flush with brickwork and slab edges. The element also has an adhesive layer (104)/peel off strip which can be used to secure the element in place prior to pouring of the concrete. The polymeric foam has an identifiable colour (105), for example, green, which can importantly be used to distinguish the present element from other products which do not contain the impregnated insecticide.

Figure 2:
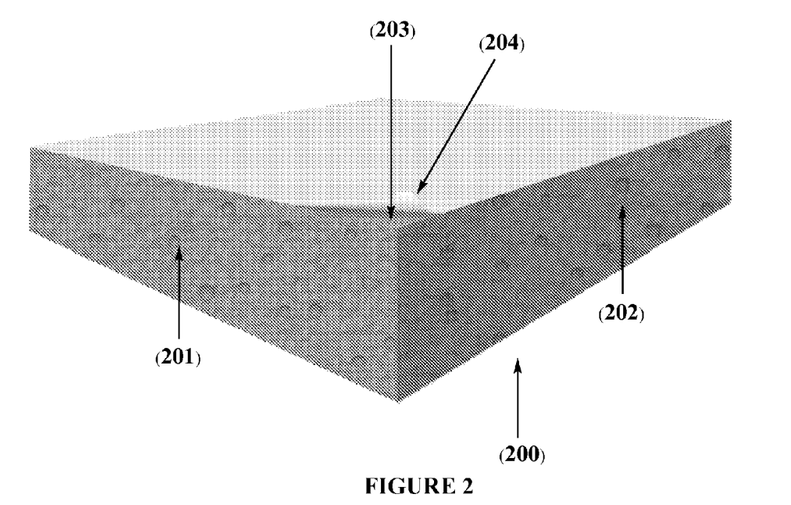
FIG. 2: Illustration of a construction element according to an embodiment of the present invention showing the removable cover

Referring to FIG. 2, an alternative embodiment of a construction element (200) is shown with the insecticide (201) distributed evenly throughout the compressible polymeric expansion joint foam (202). The water resistant adhesive (203) and the removable cover strip (204) which can be removed and the construction element secured prior to the pour of the concrete.

Figure 3:
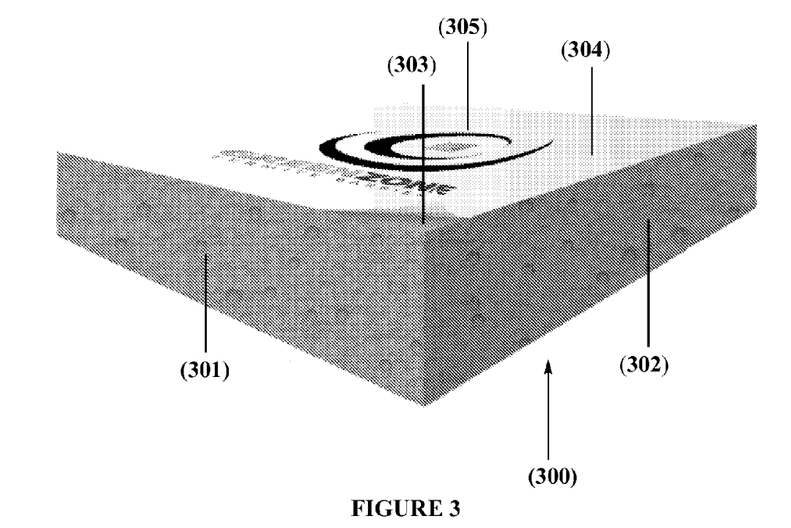
FIG. 3: Illustration of a construction element according to an embodiment of the present invention showing the removable cover and descriptive motif

Referring to FIG. 3, in this embodiment of a construction element (300), bifentrhin particles (301) are shown evenly distributed through the polyethylene-EVA polymeric composite foam (302). The water resistant adhesive (302) is shown with the cover strip (304) slightly pulled off. The distinctive motif (305) is also shown printed onto the cover strip.

Figure 4:
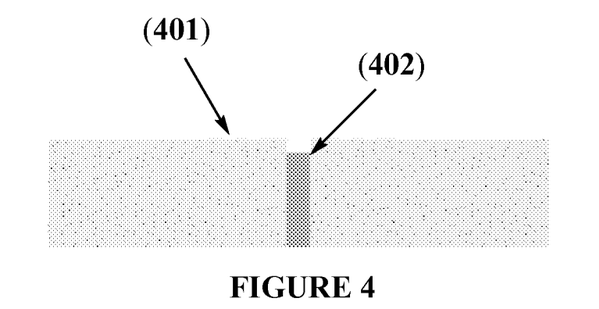
FIG. 4: Illustration of the use of the construction element according to one embodiment of the present invention and its use as in control joint.

Referring to FIG. 4, the use of a construction element (402) as a control joint is illustrated. In another embodiment, not shown, the construction element may have a flange which extends out into the concrete (401) to provide better sealing between the concrete and construction element.

Figure 5:
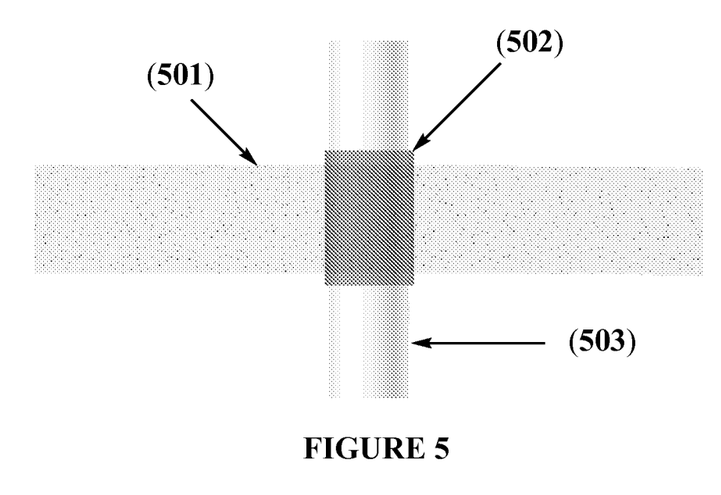
FIG. 5: Illustration of the use of the construction element according to one embodiment of the present invention as a penetration wrap around a utility pipe

Referring to FIG. 5, a construction element (502) is shown as a tube which surrounds a utility pipe (503) and provides a physical and chemical barrier to the ingress of insects, particularly termites between the pipe and concrete (501). The tubes may be manufactured to suite the size of common plumbing, services pipes or conduits. In an alternative embodiment, the expansion foam may also be applied as a wrap using the adhesive to hold it in place.

Figure 6:
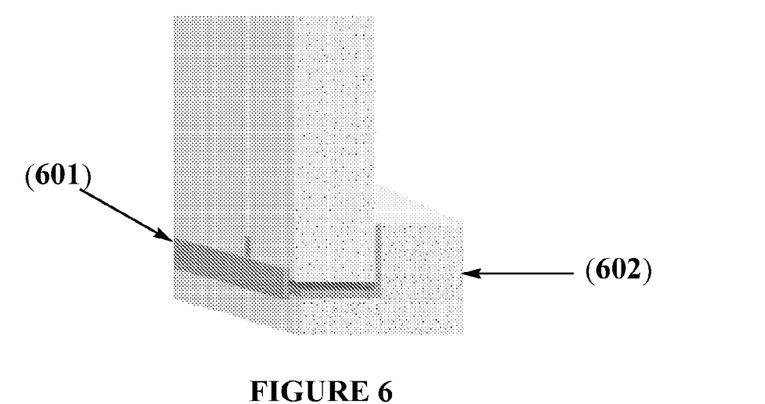
FIG. 6: Illustration of the use of the construction element according to one embodiment of the present invention in the construction of a concrete panel

Referring to FIG. 6, according to one embodiment, a construction element (601) is illustrated being used during the construction of a concrete panel (602).

Figure 7:
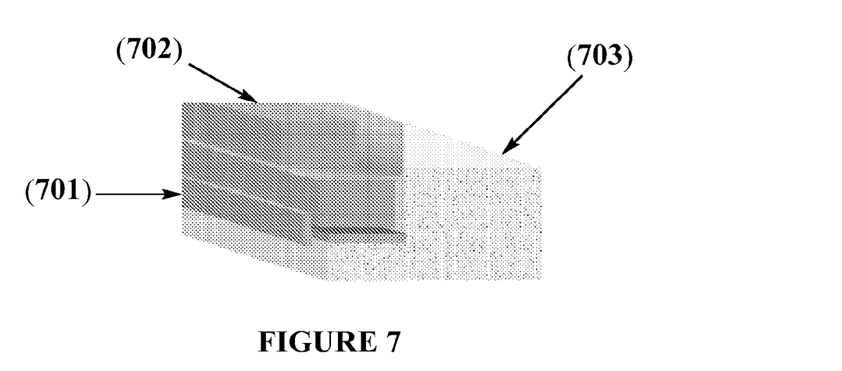
FIG. 7: Illustration of the use of the construction element according to one embodiment of the present invention as a perimeter barrier

Referring to FIG. 7, a construction element (701) is shown being used as a perimeter barrier during the construction of a concrete wall (702) and a concrete slab (703).

Figure 8:
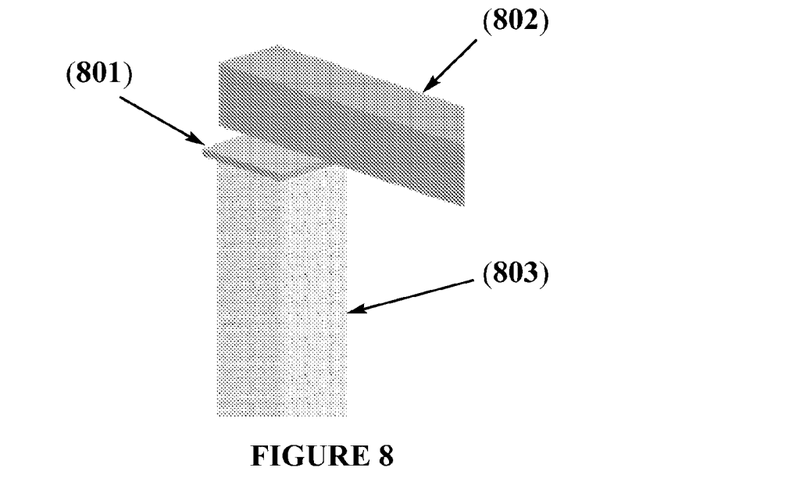
FIG. 8: Illustration of the use of the construction element according to one embodiment of the present invention as a stump cap

Referring to FIG. 8, a construction element (801) is shown being used as a stump capping between a concrete stump (802) and a wooden bearer (802). In this embodiment, the polymeric foam acts as an expansion joint.

The present invention provides a construction element for forming an expansion joint, wherein the construction element acts as a physical and chemical barrier to impede the ingress of insects into a structure, the construction element which may comprise a polymeric foam containing at least one insecticide substantially distributed throughout the polymeric foam;

wherein the polymeric foam has a cell size of approximately 0.5 mm to 2 mm.

Both open and closed cell and a combination of both open and closed cell could be used. In one preferred embodiment, the polymeric foam may comprise a closed cell polymeric foam.

In one embodiment, at least one outer surface of the construction element there is a water resistant adhesive attached thereto and a removable cover releasably attached to the adhesive whereby the removable cover is adapted to be removed upon application of the construction element. The removal of the cover allows the construction element to be secured prior to application of concrete. This is particularly useful when using the construction element to impede the ingress of insects into structures through the utility penetrations.

The removable cover may include a motif to clearly identify the construction element. The motif may comprise word(s), logo, decorative design or novel construction element characteristic.

The present invention also provides a construction element for forming an expansion joint in concrete, wherein the construction element acts as a physical and chemical barrier to impede the ingress of insects into a structure, the construction element which may comprise a closed cell polymeric foam containing at least one insecticide substantially distributed throughout the polymeric foam;

wherein the polymeric foam has a cell size of approximately 0.5 to 2 mm; and wherein on at least one outer surface of the construction element there is a water resistant adhesive attached thereto and a removable cover releasably attached to the adhesive whereby the removable cover is adapted to be removed upon application of the construction element.

The present invention also provides a construction element for forming an expansion joint, wherein the construction element acts as a physical and chemical barrier to impede the ingress of insects into a structure, the construction element which may comprise a closed cell polymeric foam containing at least one insecticide substantially distributed throughout the polymeric foam;

wherein the polymeric foam has a cell size of approximately 0.5 to 2 mm; and wherein on at least one outer surface of the construction element there is a water resistant adhesive attached thereto and a removable cover releasably attached to the adhesive whereby the removable cover is adapted to be removed upon application of the construction element.

In one embodiment, the construction element is used for forming an expansion joint in concrete.

The water resistant adhesive may include at least one insecticide therein.

In one embodiment, the polymeric foam could have a fine cell size between approximately 0.5 mm and 1 mm for even diffusion properties.

The polymeric foam may be approximately 0.5 to 30 mm thick, but could be provided in any thickness as designated in construction detailing. In one preferred embodiment, the polymeric foam is approximately 10 mm thick. For use in brick veneer constructions (in between bricks), the polymeric foam is approximately 0.5 to 6 mm thick. For use around utility penetrations, such as a pipe, the construction element may be prepared in the form of a 10 to 20 mm (but may be greater or less thickness dependent on construction detailing) thick tubes in various diameters to correspond to utility pipes, including plumbing pipe diameters, mostly in either a continuous tube (cut to length on site) or in various pre-cut lengths probably about 300 mm.

In some embodiments, the polymeric foam is between approximately 50 and 300 mm wide, preferably 100 and 200 mm wide and most preferably approximately 100 mm wide.

The polymeric foam may be manufactured from at least one polymer selected from the group which may comprise polyamide, polyvinylchloride, polyethylene, polystyrene, synthetic rubber, polymethacrylate, polypropylene, EVA polymer and polyurethane. The polymeric foam may be manufactured primarily of polyethylene, a low density polyethylene, preferably a linear low density polyethylene (LLDPE). Preferably, the polymeric foam is a crosslinked LLDPE.

In one embodiment, the polymeric foam may be comprised of primarily of linear low density polyethylene (LLPDE) or polypropylene, the foam may be open cell, closed cell, contain both open and closed cells, or may be formed as a plurality of coalesced strands or profiles depending on the needs of the application. Preferably, the polymeric foam is a closed cell LLPDE with a cell size of between approximately 0.5 mm to 2 mm. Preferably, the polymeric foam has a cell size from approximately 0.5 mm to 1 mm. The polyethylene foam preferably has a density of at least 25 kg/m$^3$ to approximately 30 kg/m$^3$. Preferably at least 16 kg/m$^3$, most preferably at least 23 to 28 kg/m$^3$.

It has been also been found that the temperature of the extrusion step can be controlled by the addition of a quantity of a secondary polymer. For example, the extrusion temperature can be kept below approximately 180° C. by adding a quantity of low melting ethylene-vinyl acetate (EVA) copolymer. The addition of low melting EVA has also been found to help in the dispersion and melt mixing of the polymer and the insecticide.

In one preferred embodiment, the polymeric foam is a composite which may comprise LDPE and low melting EVA polymer.

The polymeric foam may further comprise one more additives selected from the group which may comprise inorganic fillers, pigments, stabilizers, antioxidants, antifungal agents, acid scavengers, ultraviolet absorbers, flame retardants, processing aids, dispersion aids, extrusion aids, and the like.

In addition, other additives with insecticidal repellent and/or synergistic properties, such as piperonyl butoxide, may be added to the foamable polymer composition prior to foaming, or may be applied to the exterior portion of the foam sheet in a post-treatment process. In one embodiment, the lubricant is a food wax.

In particular, the polymeric foam may contain a UV stabilizer/UV absorbers to prevent break down of the construction element when exposed to sunlight. This is important in maintaining the longevity of the construction element which may be in place for extended periods of time.

Pigment may be added to the polymeric composition prior to foaming to given the polymeric foam a specific colour, for example green. This is important feature as it will provide a visual aid to workers to distinguish construction elements which contain an insecticide.

In the preparation of foams in accordance with the present invention, it is often desirable to add a nucleating agent to reduce the primary cell size. Preferred nucleating agents include inorganic substances such as hydrated magnesium silicate (talc), calcium carbonate, calcium silicate, indigo, talc, clay, titanium dioxide, silica, calcium stearate, diatomaceous earth, mixtures of citric acid and sodium bicarbonate, and the like. The amount of nucleating agent employed may range from about 0.01 to about 5 parts by weight per hundred parts by weight of a polymer resin. The preferred range is from 0.1 to about 3 parts by weight. The average cell size is preferably at least 0.01 mm, more preferably at least 0.1 mm, most preferably at least 0.15 mm; but is preferably no greater than 5 mm, more preferably no greater than 3 mm, and most preferably no greater than 1 mm.

In one preferred embodiment, the nucleating agent used during the blowing of the polymer is a hydrated magnesium silicate (talc). The talc may be present in an amount between approximately 0.7 to approximately 1.2 wt. % of the polymeric foam, preferably approximately 0.8 wt. %. High aspect ratio minerals, such as talc and clays, are useful nucleating agent to nucleate the gas bubbles. Talc levels >1.0 wt. % can adversely affect foaming and foam stability, therefore, the talc levels used preferably less than 0.8%.

The stabilizing agent may also be present in 0.1-10 wt. % and is one or more stabilizers is selected from the group which may comprise inorganic silicate, silicone dioxide, hydrophobic silicone dioxide, montmorillonite clay, sodium bentonite clay with high montmorillonite content, kaolin, kaolinite, magnesium aluminium silicate and aluminium silicate.

The stabilizing agent may be a high surface area inorganic silicate, preferably a high surface area aluminium silicate, for example, kaolin. During the extrusion of the masterbatch, kaolin is added as a high surface area support for Bifenthrin and as a stabilizing agent. Also during the foam of the polymer a food grade wax is added as a processing aid.

In the preparation of the expansion foam, the blowing agent may be added to the resin in any convenient manner. In an extrusion process, the blowing agent mixture is pumped into the polymeric resin and admixed therewith prior to extrusion through a die to form foam. The blowing agent may be admixed and pumped as a combination stream into the heat plastified resin, or they may be supplied as separate streams. Adequate mixing of the blowing agents into the heat plastified resin is required in order to obtain a product of desirable uniformity. Such mixing may be accomplished by a variety of means including dynamic mixers such as extruders, so-called static mixers or interfacial surface generators. For example, the blowing agent may be butane or pentane.

The insecticide may be any active agent that exhibits control or repellent affects against insect species, particularly termites.

The insecticide may also be non-repellents such as the neonicotinoid imidacloprid, Fiprinol and naturally occurring substances, such as those found in termite resistant trees, such as those found in Red Gum trees, *Eucalyptus camaldulensis*.

The insecticide(s) which is impregnated in the polymeric material may be any active agent that exhibits control or repellent affects against insect species, particularly termites. The active agent(s) may include, but are not limited to, pyrethrum, synthetic pyrethroids, organo-chlorines, organo-sulfurs, carbamates, organo-phosphates, formamidines, nicotinoids, spinosyns, phenylpyrazoles, pyrroles, pyrazoles, dinitrophenols, pyridazinones, quinazolines, and benzoylureas. Preferably, a noted termiticide is used such as bifenthrin, permethrin, deltamethrin, lambda-cyhalothrin, cypermethrin, alpha-cypermethrin, zeta-cypermethrin, tetramethrin, and cyfluthrin.

The term "pyrethrum" as used herein means pyrethrin compounds derived from chrysanthemum plants, or the same or similar compounds derived from other natural sources, and pyrethroid compounds manufactured synthetically. Specific examples of such compounds include, but are not limited to, deltamethrin, permethrin, cypermethrin, ifenthrin, cyfluthrin, cyhalothrin, tefluthrin, resmethrin, allethrin, kadethrin, sanmarton, fenvalerate, esfenvalerate, lambda-cyhalothrin, tralomethrin, fenpropathrin, tetramethrin, as well as mixtures thereof. These compounds may be extracted from plant sources or may be prepared by a suitable chemical process, and are commercially available from such sources as AgrEvo, Zeneca, Bayer, FMC Corporation, and Aldrich Chemical. Preferably, the compound is a pyrethroid compound selected from deltamethrin, permethrin, bifenthrin, and mixtures thereof. In a particular embodiment, the insecticide bifenthrin is used. Bifenthrin has a non-alpha-cyano molecular structure which renders it a dermal non-sensitiser, i.e. does not react substantially with a person's skin.

The pyrethrum and synthetic pyrethroid family of compounds have very effective surface contact insect repellence, which is important to the prevention of insect attack to any foam products which contains them. The thermal and chemical stability and structure of pyrethrum and synthetic pyrethroid compounds adds to their suitability in plastic manufacturing processes. After manufacture, many pyrethrum and synthetic pyrethroid compounds remain encapsulated in the foam plastic resin because of their chemical structure and relatively low vapour pressure. As a result, the pyrethrum and synthetic pyrethroid compounds provide long-term protection against insect borings that could affect the physical properties of the foam. The concentration of pyrethrum and synthetic pyrethroid compounds in the foam that provides the desired efficacy depends on the specific material used and the targeted insect.

In general, the insecticide, in particular the pyrethrum and synthetic pyrethroid compounds are preferably employed in a cumulative amount. For example, during the preparation of the masterbatch the insecticide, for example bifenthrin, is added at a concentration (wt. %) of the polymer of between approximately 10 to 20 wt. %. Preferably, the percentage bifenthrin in the masterbatch is 20 wt. %. Upon extrusion and foaming, the eventual concentration of the bifenthrin in the foam is between approximately 0.2 to 2 wt. %, preferably, approximately 1 wt %.

The insecticide(s) is dispersed, preferably evenly, substantially throughout the polymer matrix of the expansion foam. For example, bifenthrin may be introduced in a powder form and incorporated into the LLPE-EVA resin masterbatch. Depending on the product, the active agent could be added as granules, powder form or liquid to be incorporated into the polymeric foam. Preferably, the insecticide does not leach from the polymeric foam.

In one embodiment, the active agent(s) may be selected from any one or more of the group which may comprise pyrethrum, synthetic pyrethroids, organo-chlorines, organo-sulfurs, carbamates, organo-phosphates, formamidines, nicotinoids, spinosyns, phenylpyrazoles, pyrroles, pyrazoles, dinitrophenols, pyridazinones, quinazolines, and benzoylureas.

The synthetic pyrethroid compound may be selected from the group which may comprise deltamethrin, permethrin, bifenthrin, and mixtures thereof.

Preferably, the at least one insecticide is a termiticide.

In a preferred embodiment, the synthetic pyrethroid is bifenthrin. In one embodiment, the bifenthrin is added as 0.5 wt. % of the polymeric foam. The exact concentration used may depend on the type of expansion joint, targeted insect and the climatic conditions. The inclusion of bifenthrin in the polymeric foam provides a repellent barrier as well as a chemical barrier to the penetration of termites.

In one embodiment, the expansion foam is a closed cell polyethylene with a density between 23 to 28 $kg/m^3$.

In one embodiment, the polymeric foam has a density of between 23 to 28 $kg/m^3$, preferably 25 $kg/m^3$.

The polymeric foam has a tear strength of greater than 2.5 $kg/cm^2$, preferably between approximately 2.5 to 4 $kg/m^2$.

In one embodiment, the polymeric foam used to prepare the construction element has a compression set at 22 hours of less than 10%. Preferably, the compression set at 22 hours of less than 6%.

In a preferred embodiment, the polymeric foam has an elongation of greater than 140%.

The tensile strength of the polymeric foam may be greater than 2.5 $kg/m^2$ (0.245 MPa)

When a new concrete slab is poured, it should be recognized that the concrete may form an intimate seal with the utility penetration. However, this is not always the case. If the utility penetration is moved during concrete pour then a gap may be opened through the slab. Also it is common plumbing practice to put plastic sleeving or foam (for example, polyurethane) around pipes to allow for expansion and to prevent contact of copper pipes with cement. Both of these practices may lead to crawling pests-sized gaps. Also during the lifetime of the slab, it is exposed to many pressures, including expansion and contraction of the concrete, expansion and contraction of the pipes, all of which may lead to gaps opening near utility penetrations.

In one embodiment, the construction element according to the present invention may be used around utility penetrations which occur in all forms of concrete slabs and sometimes the walls of buildings prior to pouring a concrete foundation.

This aspect of the invention provides means for creating a barrier around an elongated member of a utility penetration. Such elongated members include, but are not limited to, plumbing and utility supply pipes, gas lines, electrical wiring, and conduits. The element of the present invention when installed, prevent the formation of significant gaps between the device and a utility penetration, and between the device and the concrete layer.

In one embodiment, the present invention provides a method of protecting a structure against the ingress of insects into the structure, the method which may comprise the step of positioning one or more construction element(s) at a position (s) during the construction of the structure to form a barrier to at least impede the entry of insects, the construction element which may comprise a closed cell polymeric foam containing at least one insecticide substantially distributed throughout the polymeric foam;
wherein the polymeric foam has a cell size of approximately 0.5 to 2 mm; and
wherein on at least one outer surface of the construction element there is a water resistant adhesive attached thereto and a removable cover releasably attached to the adhesive whereby the removable cover is adapted to be removed upon application of the construction element.

In one embodiment, the step of positioning the construction elements involves placing construction element(s) around a utility penetration(s), such as pipes, and subsequently pouring the concrete slab. With this embodiment, the construction element may be provided in the form of a tube which has a tube inside diameter of slightly larger than the utility penetration to allow a snug fit with the utility. Alternatively, the construction element may be provided as a sheet which is cut to size on-site and the adhesive layer used to secure the construction element to the utility when pouring the concrete.

In another embodiment, the construction element may be used as a stump cap between a concrete stump and the wooden parts of the construction, including the bearer, floor joists and floor.

In another embodiment, the construction element may be used as a perimeter barrier during the construction of a concrete wall and a concrete slab.

In some embodiments, the expansion foam of the present invention may include the following features:
Can be supplied in any length, for example, 25 m rolls for ease of use and transport on site
Can be any width, for example, 100 mm width, with other variations in lesser amounts
150 mm
200 mm
300 mm Mostly in 10 mm depth but could also be:
0.5-6 mm for use in brick veneer construction (in between bricks)
0.5-20 mm thick tubes in various diameter to correspond to plumbing pipe diameters; mostly in either a continuous tube (cut to length on site) or in various lengths probably about 300 mm.
Using a specific colour for branding and branded sticky back paper Foam Characteristics It is desirable that the expansion foam(s) of the present invention have the following characteristics:
Compression set (22 hrs)<6% to max of <10%
Target density of 25 g/cc
Tear strength>2.5 kg/cm$^2$
Elongation>140%
Tensile strength>2.5 kg/cm$^2$
Production at less than 180° C.

Examples of these situations where the construction element of the present invention may be used include any one or more of the following:

Plumbing and electrical pipes which are installed prior to a slab being poured and which protrude through the slab once it is poured are 'lagged' with foam by plumbers and electricians to protect the pipes, absorb pressure and allow for the contraction and expansion of slabs that occurs as they set, are subjected to environmental changes and physical pressures of weight loading once they are built on.

Where concrete slabs for large construction are achieved in multiple, staged pours these contraction, expansion and load pressures are managed by the installation of expansion joint foam in between slab pours which allows for movement in the slab.

Other concrete slab floors are achieved by pouring 'in-fill slabs'. This is usually where concrete, pre-cast tilt panels are stood or block and brick work walls are built for external and internal walls and then the concrete floor is poured filling the void in between the walls. These walls and tilt panels require expansion joint foam to be installed along their base Where tilt panels are stood on top existing concrete slabs.

Extensions are often poured to immediately abut existing structures and concrete, the area where these two structures meet also requires the installation of expansion joint foam to absorb pressure.

Concrete and paving are also frequently poured immediately abutting new house slabs in a secondary pour, usually for a garage, pathway, patio, air-conditioning and water tank stands. In these instances expansion joint foam between the existing and new slab or paving is applied to absorb pressure and allow for contraction and expansion.

The construction element of the present invention may be a pre-shaped flexible foam, which may be cut and shaped into a variety of shapes and sizes to suit a particular application.

In some embodiments, the construction element of the present invention may include the following characteristics:
Incorporates an active Termiticide ingredient, preferably Bifenthrin at 1% concentration;
Incorporates the Termiticide into a 'masterbatch' of silicate resin Polyethylene at 10% concentration;
Masterbatch is then incorporated into standard PE resin;

Closed cell, cross linked PE foam is produced using an extrusion process at a specified temperature;

Foam is then cut to size and shape depending on the final product composition (varying lengths, widths, depths and some production for use as a tube or cylinders of varying diameter)

Post production application of an adhesive strip (with backing paper) and a partial tearaway or zip strip for neat finishing Products which could be made from the construction elements include:

A 'sock' for slab penetrations, a tube that is installed by simply pulling over plumbing pipes;

A rolled length for use in construction joins and perimeter applications; and

A wider, thinner foam, with greater tensile strength properties for use in brick veneer and block work perimeters.

Examples of these situations where the construction element may be used include:

Plumbing and electrical pipes which are installed prior to a slab being poured and which protrude through the slab once it is poured are 'lagged' with foam by plumbers and electricians to protect the pipes, absorb pressure and allow for the contraction and expansion of slabs that occurs as they set, are subjected to environmental changes and physical pressures of weight loading once they are built on.

Where concrete slabs for large construction are achieved in multiple, staged pours these contraction, expansion and load pressures are managed by the installation of expansion joint foam in between slab pours which allows for movement in the slab.

Other concrete slab floors are achieved by pouring 'in-fill slabs'. This is usually where concrete, pre-cast tilt panels are stood or block and brick work walls are built for external and internal walls and then the concrete floor is poured filling the void in between the walls. These walls and tilt panels require expansion joint foam to be installed along their base Where tilt panels are stood on top existing concrete slabs Extensions are often poured to immediately abut existing structures and concrete, the area where these two structures meet also requires the installation of expansion joint foam to absorb pressure.

Concrete and paving are also frequently poured immediately abutting new house slabs in a secondary pour, usually for a garage, pathway, patio, air-conditioning and water tank stands. In these instances expansion joint foam between the existing and new slab or paving is applied to absorb pressure and allow for contraction and expansion.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

NON-LIMITING EXAMPLES

The present invention is described in greater detail below with the aid of the following non-limiting examples. The percentages are given by weight unless otherwise stated. It goes without saying, however, that these examples are given by way of illustration of the invention and do not constitute in any manner a limitation thereto.

Example 1

Thermogravimetric Study of the Stability of Bifenthrin

In order to determine whether extrusion-based masterbatch preparation was possible without excessive thermal decomposition or volatilization of bifenthrin, a thermogravimetric study was performed using a thermal balance.

It was found that degradation of the active occurs at about 180° C. and that provided LLDPE is used as the polyethylene carrier resin then extrusion temperatures can be utilized to keel just below this threshold temperature of decomposition.

Example 2

Masterbatch (mb) Preparation

A masterbatch polymeric carrier resin was prepared by melt mixing bifenthrin (10% wt. percentage), low melting EVA polymer and either a high melt index linear low density polyethylene (LLDPE) or low density polyethylene (LDE). It was found that in order to assist in the absorption and retention of the Bifenthrin, a high surface area inorganic silicate additive was also added to melt, for example kaolin.

In this way, 10% of the active bifenthrin was incorporated into an EVA-LLDPE-silicate carrier resin and masterbatch pellets produced. The active was found to be properly encapsulated and there were no measurable evaporative losses.

A 20% bifenthrin masterbatch can also be prepared by adjusting the concentration of bifenthrin

Example 3

Foam Preparation

The following masterbatch loadings may be prepared:

Given a 10% masterbatch (mb) to produce the following active levels the following mb add rates are required:

0.25% active constituent (2.5% mb add rate)
0.5% active constituent (5% mb add rate)
0.75% active constituent (7.5% mb add rate)
1.0% active constituent (10% mb add rate)

The specifications for the target foam are:

Target density of 25 g/cc
Tear strength>2.5 kg/cm$^2$
Compression set (22 hrs)<6%
Elongation>140%
Tensile strength>2.5 kg/cm$^2$ Compression Set is a permanent partial loss of initial height of a flexible polyethylene foam sample after compression due to a bending or collapse of the cell.

For the target application the foam requires a maximum compression set, <10%.

A standard foam extruder was used to prepare the polymeric foam. For example, talc can be added as a nucleating agent and blowing agents such as butane or pentane injected. A processing aid can also be added, generally a food grade wax is used. The foaming grade polymer used is generally a foaming grade polyethylene, for example Cosmothene F210.

Example 4

Application to a Utility Pipe

Prior to installation of the construction element, the construction site is prepared for the installation of a foundation including the placement of utility penetrations, such as pipes. The construction element is wrapped around the elongated member of the pipe until the pipe is firmly in contact with the element. The construction element may be held in place by the water resistant adhesive until the concrete slab is poured. This ensures intimate contact is made between the utility penetration and the construction element.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

APPENDIX A

Termite Solution

This invention is a new and unique termite barrier both in constructed materials and application process. This invention relates to the building, construction and pest control industries.

The Termite Solution invention impregnates a cross linked polyethylene strip material with a termiticide to create a new product that functions and is applied in a similar manner to foam expansion joint strips but that also acts as physical and chemical termite barrier in compliance with the related Australian Standard.

This invention also creates a single product system which does not require component parts (i.e. silicone, collars and physical or chemical barriers). The product also fulfills the function of a foam expansion joint strip and its usual applications within construction.

The Termite Solutions was invented after years of practical experience within the industry and with the difficulties and limitations of existing termite barriers both in terms of application and function of the product and also the need for builders to engage a pest control company to install the barrier.

The main problems experienced with the application of existing physical and chemical barriers are outlined below. This invention aims to address these problems as outlined in the table below.

| Current Product and Application Difficulties | Termite Solution |
| --- | --- |
| When installing a physical barrier such as Kordon or Homeguard (chemically impregnated plastic sheet) we often had to remove builders foam expansion joint strips to install the barrier and then replace the expansion joint stripping again. This duplicated effort unnecessarily. | By incorporating the form and function of a foam expansion joint strip, installers avoid duplication of effort and experience a cost saving by installing one product/process rather than two. |
| Difficulties faced in installing the above products also included applying them on exposed work sites where they were affected by weather and winds (i.e. the product would flap around and move during installation and liquid chemicals could not be installed during inclement weather (i.e. rain or pooling of water on site). | By including; an adhesive strip, range of widths and lengths, being lightweight, flexible and water resistant Termite Solution can be installed more easily by a single installer and in any weather condition |
| Most termite systems require the use of multiple products to create a complete and compliant system, therefore installers had to stock and carry silicone, a wide variety of sizes of pipe penetration collars and the physical barrier | Termite Solution is a single product system that will comply with requisite Australian Standards and legislative requirements (accreditation and codemark to be applied for) The foam stripping can be applied to tilt panel bases, construction joins, pipe penetrations and building perimeters. There is no need to use multiple products and their accessories. It is one size fits all. |
| The installation process of existing physical products and chemical barriers requires the engagement of licensed pest controller. This usually requires the scheduling of works in conjunction with a builders often fluctuating construction schedule especially as it relates to the preparation of concrete slabs and tilt panel lifts. It was often considered a nuisance or hassle to have to liaise with and schedule the licensed pest controller to be on site when required and often led to delays in the construction schedule | Termite Solution will be able to be installed by accredited builders as well as pest controllers as it does not require a pest control license to use, store or handle. As such builders who are accredited can maintain a stock on site Where Certification is required by local government authorities the installer sends a site plan, marked with installation points and a statement that it was installed as per manufacturer's instructions to a central administration point and receives a Certificate of Installation to meet local government requirements |

Technical Features
  Key technical features are:
  Termiticide impregnated cross linked, closed cell, polyethylene or like substance that termites cannot forage on or breach (1)
  The planned termiticide is a generic Bifenthrin in required volumes to meet Australian and International Standards
  The termiticide will kill and repel termites created a physical and chemical barrier (min 10 yrs to unlimited shelf life, actual product lifespan to be determined through testing) (3)
  The cross linked, closed cell polyethylene will:
    Be resistant to water absorption
    Have a wide range of working temperatures (at least −80-90° C.)
    Have an approximate density of 23-28 kg/m$^3$
    Have significant tensile strength and tear resistance (to be determined)
    Be capable of managing compressive loads (to be determined)
    Chemical resistance to fungi, soap, detergents, acid, salts and alcohol.
  Manufactured and distributed in rolls of different lengths and widths for varying applications
    A zipping strip to one top edge to create a neat finish flush with brick work (2)
    An adhesive/peel off strip to secure the product during construction (4)
    A nominated/identifiable colour to distinguish it (and the MSDS implications) from foam expansion joint stripping (5)
    A nominated/identifiable logo and branding to distinguish it from other products
  At this stage of product development no preferred or optional features are nominated although this may change after research and consultation.
  Exact product specifications, dimensions and chemical concentrations are to be developed in consultation with technical experts, chemical suppliers and product manufacturers under commercial confidentiality agreements within the 12 month period of the provisional patent. However we expect product development to market commercialisation to take a longer time than 12 months due to environmental testing required proving suitability and durability for purpose, hence the application for a standard patent.
  Application of Termite Solution will involve:
    Determining requisite points of installation as it relates to the Australian Standard and nominated construction methods
    Usual application will include to pipe and slab penetrations by wrapping the product around each pipe penetrations and securing using included adhesive strip, application to construction joins/saw cuts, application to base of tilt slabs and/or external perimeter of concrete slab as required
    Where required by legislation (only some local governments require product) submission of requisite forms and statements to secure a Certificate of Installation
  The invention is further described by the following numbered paragraphs:
  1. A construction element for forming an expansion joint, wherein the construction element acts as a physical and chemical barrier to impede the ingress of insects into a structure, the construction element comprising
    a polymeric foam containing at least one insecticide substantially distributed throughout the polymeric foam;
    wherein the polymeric foam has a cell size of approximately 0.5 to 2 mm; and
    wherein on at least one outer surface of the construction element there is a water resistant adhesive attached thereto and a removable cover releasably attached to the adhesive whereby the removable cover is adapted to be removed upon application of the construction element.
  2. The construction element according to paragraph 1, wherein the polymeric foam is closed cell polymeric foam.
  3. The construction element according to paragraph 1 or paragraph 2, wherein the polymeric foam has a cell size of approximately 0.5 mm to 1 mm.
  4. The construction element according to any one of the preceding paragraphs, wherein the polymeric foam is approximately 0.5 to 30 mm thick.
  5. The construction element according to paragraph 1 or paragraph 2, wherein the polymeric foam is approximately 10 mm thick.
  6. The construction element according to any one of the preceding paragraphs, wherein the polymeric foam is manufactured from at least one polymer selected from the group comprising polyamide, polyvinylchloride, polyethylene, polystyrene, synthetic rubber, polymethacrylate, polypropylene, EVA polymer and polyurethane.
  7. The construction element according to paragraph 6, wherein the polymeric foam may be manufactured primarily of polyethylene, preferably a linear low density polyethylene (LLDPE).
  8. The construction element according to paragraph 7, wherein the polymeric foam is a composite comprising LLDPE and low melting EVA polymer.
  9. The construction element according to any one of the preceding paragraphs, wherein the polymeric foam further comprises one more additives is selected from the group inorganic fillers, pigments, lubricants, stabilizers, antioxidants, antifungal agents, acid scavengers, ultraviolet absorbers, flame retardants, processing aids, dispersion aids, extrusion aids, and the like.
  10. The construction element according to paragraph 9, wherein the stabilizing agent is present in 0.1-10 wt. % and is one or more stabilizers is selected from the group comprising inorganic silicate, silicone dioxide, hydrophobic silicone dioxide, montmorillonite clay, sodium bentonite clay with high montmorillonite content, magnesium aluminium silicate and aluminium silicate.
  11. The construction element according to paragraph 9, wherein the stabilizing agent is a high surface area inorganic silicate, preferably kaolin.
  12. The construction element according to any one of the preceding paragraphs, wherein the insecticide is any active agent that exhibits control or repellent affects against insect species, particularly termites.
  13. The construction element according to paragraph 12, wherein the active agent(s) is selected from any one or more of the group comprising pyrethrum, synthetic pyrethroids, organo-chlorines, organo-sulfurs, carbamates, organo-phosphates, formamidines, nicotinoids, spinosyns, phenylpyrazoles, pyrroles, pyrazoles, dinitrophenols, pyridazinones, quinazolines, and benzoylureas.
  14. The construction element according to paragraph 13, wherein the synthetic pyrethroid compound is selected from the group comprising deltamethrin, permethrin, bifenthrin, and mixtures thereof.
  15. The construction element according to paragraph 14, where in the synthetic pyrethroid is bifenthrin.
  16. The construction element according to any one of the preceding paragraphs, wherein the concentration of the insecticide is between approximately 0.25 to 2.0 wt. %, more preferably approximately 0.5 wt. %, more preferably 0.75 wt. % and more preferably 1 wt. %.

17. The construction element according to any one of the preceding paragraphs, wherein the polymeric foam has a density of between 23 to 28 kg/m³, preferably 25 kg/m³.

18. The construction element according to any one of the preceding paragraphs, wherein the polymeric foam has a tear strength of between approximately 2.5 to 4.0 kg/cm², preferably greater than approximately 2.5 kg/cm².

19. The construction element according to any one of the preceding paragraphs, wherein the polymeric foam has a compression set at 22 hours of less than 6%.

20. The construction element according to any one of the preceding paragraphs, wherein the polymeric foam has an elongation of greater than 140%.

21. The construction element according to any one of the preceding paragraphs, wherein the removable cover includes a motif.

22. The construction element according to paragraph 21, wherein the motif comprises words, logo, decorative design or novel construction element characteristic.

23. The construction element according to any one of the preceding paragraphs, which includes at least one zipping strip to one top edge of the polymeric foam.

24. The construction element according to any one of the preceding paragraphs, wherein the polymeric foam includes a UV stabilizer.

25. Use of the construction element according to any one of the preceding paragraphs for the preparation of a construction joint, penetration wrap around a utility pipe, tube to be applied to utility pipes, concrete panel, perimeter barrier and a stump cap.

26. A method of protecting a structure against the ingress of insects into the structure, the method comprising the step of positioning one or more construction element(s) at a position (s) during the construction of the structure to form a barrier to at least impede the entry of insects, the construction element comprising
    a polymeric foam containing at least one insecticide substantially distributed throughout the polymeric foam;
    wherein the polymeric foam has a cell size of approximately 0.5 to 2 mm; and
    wherein on at least one outer surface of the construction element there is a water resistant adhesive attached thereto and a removable cover releasably attached to the adhesive whereby the removable cover is adapted to be removed upon application of the construction element.

27. A construction element substantially as hereinbefore described.

28. Use of a construction element substantially as hereinbefore described.

29. A method of impeding the ingress of insects into a structure substantially as hereinbefore described.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A construction element capable of forming an expansion joint, the construction element comprising
    a polymeric foam containing at least one insecticide substantially distributed throughout the polymeric foam;
    wherein the polymeric foam has a cell size of approximately 0.5 to 2 mm; and
    wherein on at least one outer surface of the construction element there is a water resistant adhesive attached thereto and a removable cover releasably attached to the adhesive whereby the removable cover is adapted to be removed upon application of the construction element;
    wherein the construction element acts as a physical and chemical barrier to impede the ingress of insects into a structure;
    wherein the polymeric foam has a compression set at 22 hours of less than 6%;
    wherein the polymeric foam is closed cell polymeric foam;
    wherein the polymeric foam is manufactured at a temperature of less than 180° C. and is prepared primarily from a blend of a crosslinked polyethylene and a low melting ethylene-vinyl acetate (EVA) copolymer; and
    wherein the polymeric foam has a density of between 23 to 28 kg/m³.

2. The construction element according to claim 1, wherein the polymeric foam has a cell size of approximately 0.5 mm to 1 mm.

3. The construction element according to claim 1, wherein the polymeric foam is approximately 0.5 to 30 mm thick.

4. The construction element according to claim 1, wherein the polymeric foam is approximately 10 mm thick.

5. The construction element according to claim 1, wherein the crosslinked ethylene is a crosslinked linear low density polyethylene (LLDPE).

6. The construction element according to claim 1, wherein the polymeric foam is a composite comprising crosslinked LLDPE and low melting EVA polymer.

7. The construction element according to claim 1, wherein the polymeric foam comprises a stabilizer and the stabilizer is kaolin.

8. The construction element according to claim 1, wherein the insecticide exhibits control or repellent affects against termites.

9. The construction element according to claim 1, wherein the insecticide is selected from any one or more of the group comprising pyrethrum, synthetic pyrethroids, organo-chlorines, organo-sulfurs, carbamates, organo-phosphates, formamidines, nicotinoids, spinosyns, phenylpyrazoles, pyrroles, pyrazoles, dinitrophenols, pyridazinones, quinazolines, and benzoylureas.

10. The construction element according to claim 1, wherein the insecticide is a synthetic pyrethroid compound selected from the group comprising deltamethrin, permethrin, bifenthrin, and mixtures thereof.

11. The construction element according to claim 1, wherein the insecticide is bifenthrin.

12. The construction element according to claim 1, wherein the concentration of the insecticide is selected from the group comprising between approximately 0.25 to 2.0 wt. %, approximately 0.5 wt. %, 0.75 wt. % and 1 wt. %.

13. The construction element according to claim 1, wherein the polymeric foam has a density of 25 kg/m³.

14. The construction element according to claim 1, wherein the polymeric foam has a tear strength of between approximately 2.5 to 4.0 kg/cm².

15. The construction element according to claim 1, wherein the polymeric foam has an elongation of greater than 140%.

16. The construction element according to claim 1, wherein the removable cover includes a motif.

17. The construction element according to claim 1, wherein the removable cover includes a motif and the motif comprises words, logo, decorative design or construction element characteristic.

18. The construction element according to claim 1, which includes at least one zipping strip to one top edge of the polymeric foam.

19. The construction element according to claim 1, wherein the polymeric foam includes a UV stabilizer.

20. The construction element of claim 1 wherein the polymeric foam further comprises one more additives selected from the group comprising inorganic fillers, pigments, lubricants, stabilizers, antioxidants, antifungal agents, acid scavengers, ultraviolet absorbers, flame retardants, processing aids, dispersion aids and extrusion aids.

21. The construction element according to claim 20, wherein a stabilizer is present in an amount between 0.1-10 wt. % and the stabilizers is selected from the group comprising inorganic silicate, silicone dioxide, hydrophobic silicone dioxide, montmorillonite clay, sodium bentonite clay with high montmorillonite content, magnesium aluminium silicate and aluminium silicate.

22. A method of protecting a structure against the ingress of insects into the structure, the method comprising the step of positioning one or more construction element(s) at a position(s) during the construction of the structure to form a barrier to at least impede the entry of insects, the construction element comprising
    a polymeric foam containing at least one insecticide substantially distributed throughout the polymeric foam;
    wherein the polymeric foam has a cell size of approximately 0.5 to 2 mm; and
    wherein on at least one outer surface of the construction element there is a water resistant adhesive attached thereto and a removable cover releasably attached to the adhesive whereby the removable cover is adapted to be removed upon application of the construction element;
    wherein the polymeric foam has a compression set at 22 hours of less than 6%;
    wherein the polymeric foam is closed cell polymeric foam;
    wherein the polymeric foam is manufactured at a temperature of less than 180° C. and is prepared primarily from a blend of a crosslinked polyethylene and a low melting ethylene-vinyl acetate (EVA) copolymer; and
    wherein the polymeric foam has a density of between 23 to 28 kg/m$^3$.

* * * * *